(12) United States Patent
Ni et al.

(10) Patent No.: US 12,737,618 B2
(45) Date of Patent: Sep. 15, 2026

(54) SUPERCLASS-CONDITIONAL GAUSSIAN MIXTURE MODEL FOR PERSONALIZED PREDICTION ON DIALYSIS EVENTS

(71) Applicant: NEC Laboratories America, Inc., Princeton, NJ (US)

(72) Inventors: Jingchao Ni, Princeton, NJ (US); Wei Cheng, Princeton Junction, NJ (US); Haifeng Chen, West Windsor, NJ (US)

(73) Assignee: NEC Corporation (JP)

(*) Notice: Subject to any disclaimer, the term of this patent is extended or adjusted under 35 U.S.C. 154(b) by 1029 days.

(21) Appl. No.: 17/950,203

(22) Filed: Sep. 22, 2022

(65) Prior Publication Data

US 2023/0094623 A1 Mar. 30, 2023

Related U.S. Application Data

(60) Provisional application No. 63/397,060, filed on Aug. 11, 2022, provisional application No. 63/247,335, filed on Sep. 23, 2021.

(51) Int. Cl.

*G06N 3/08* (2023.01)
*G06N 3/044* (2023.01)
(Continued)

(52) U.S. Cl.

CPC ............... *G06N 3/08* (2013.01); *G06N 3/044* (2023.01); *G06N 7/01* (2023.01); *G16H 20/10* (2018.01); *G16H 50/70* (2018.01)

(58) Field of Classification Search

CPC ............ G06N 3/08; G06N 7/01; G06N 3/044; G16H 50/70; G16H 20/10
See application file for complete search history.

(56) References Cited

U.S. PATENT DOCUMENTS 11,514,226 B2 * 11/2022 Massand ............... G06F 40/194
2020/0337625 A1 * 10/2020 Aimone ............... A61B 5/7267
(Continued)

FOREIGN PATENT DOCUMENTS

AU 2021363110 A1 * 10/2022 ........... A61B 5/7267
CN 112107752 A * 12/2020 .......... A61M 1/1613
(Continued)

OTHER PUBLICATIONS

Esteban et al., "Predicting Clinical Events by Combining Static and Dynamic Information using Recurrent Neural Networks," arXiv: 1602.02685v2 [cs.LG] Nov. 17, 2016. (Year: 2019).*
(Continued)

*Primary Examiner* — Jonathon A. Szumny
(74) *Attorney, Agent, or Firm* — Vincent Duffy

(57) ABSTRACT

A computer-implemented method for model building is provided. The method includes receiving a training set of medical records and model hyperparameters. The method further includes initializing an encoder as a Dual-Channel Combiner Network (DCNN) and initialize distribution related parameters. The method also includes performing, by a hardware processor, a forward computation to (1) the DCNN to obtain the embeddings of the medical records, and (2) the distribution related parameters to obtain class probabilities. The method additionally includes checking by a convergence evaluator if the iterative optimization has converged. The method further includes performing model personalization responsive to model convergence by encoding the support data of a new patient and using the embeddings and event subtype labels to train a personalized classifier.

17 Claims, 7 Drawing Sheets

(51) Int. Cl.

| | |
|---|---|
| ***G06N 7/01*** | (2023.01) |
| ***G16H 20/10*** | (2018.01) |
| ***G16H 50/70*** | (2018.01) |

(56) References Cited

U.S. PATENT DOCUMENTS

| | | | | |
|---|---|---|---|---|
| 2021/0098090 | A1* | 4/2021 | Thomas | G16H 50/30 |
| 2021/0125722 | A1* | 4/2021 | Sherkat | G06N 3/04 |
| 2022/0104737 | A1* | 4/2022 | Smit | A61B 5/14551 |
| 2023/0051411 | A1* | 2/2023 | Chen | G06V 10/774 |
| 2023/0080350 | A1* | 3/2023 | Nadkarni | G06N 3/0985 705/2 |
| 2024/0321447 | A1* | 9/2024 | Selvaraj | G16H 50/70 |

FOREIGN PATENT DOCUMENTS

| | | | | |
|---|---|---|---|---|
| EP | 3822876 | A2 * | 5/2021 | G01C 21/3617 |
| KR | 20200075088 | A * | 6/2020 | G16H 10/60 |

OTHER PUBLICATIONS

Esteban et al., "Predicting Sequences of Clinical Events by using a Personalized Temporal Latent Embedding Model," 2015 International Conference on Healthcare Informatics; DOI 10.1109/ICHI.2015.23. (Year: 2015).*

Putra et al., "Prediction of Clinical Events in Hemodialysis Patients sing an Artificial Neural Network," MEDINFO 2019: Health and Wellbeing e-Networks for All; doi: 10.3233/SHTI190539. (Year: 2019).*

De Bois et al., "Adversarial multi-source transfer learning in healthcare: Application to glucose prediction for diabetic people," Computer Methods and Programs in Biomedicine 199 (2021) 105874; https://doi.org/10.1016/j.cmpb.2020.105874. (Year: 2021).*

Asano, Y. M., Rupprecht, C., & Vedaldi, A. (Nov. 13, 2019). Self-labelling via simultaneous clustering and representation learning. arXiv preprint arXiv:1911.05371.

Bukchin, G., Schwartz, E., Saenko, K., Shahar, O., Feris, R., Giryes, R., & Karlinsky, L. (Jun. 20, 2021). Fine-grained angular contrastive learning with coarse labels. In Proceedings of the IEEE/CVF Conference on Computer Vision and Pattern Recognition (pp. 8730-8740).

Caron, M., Misra, I., Mairal, J., Goyal, P., Bojanowski, P., & Joulin, A. (Dec. 6, 2020). Unsupervised learning of visual features by contrasting cluster assignments. Advances in Neural Information Processing Systems, 33, 9912-9924.

Chen, X., Fan, H., Girshick, R., & He, K. (Mar. 9, 2020). Improved baselines with momentum contrastive learning. arXiv preprint arXiv:2003.04297.

Grathwohl, W., Wang, K. C., Jacobsen, J. H., Duvenaud, D., Norouzi, M., & Swersky, K. (Dec. 6, 2019). Your classifier is secretly an energy based model and you should treat it like one. arXiv preprint arXiv:1912.03263.

He, K., Zhang, X., Ren, S., & Sun, J. (Jun. 26, 2016). Deep residual learning for image recognition. In Proceedings of the IEEE conference on computer vision and pattern recognition (pp. 770-778).

Krizhevsky, A., & Hinton, G. (Apr. 8, 2009). Learning multiple layers of features from tiny images.

Lee, K., Lee, K., Lee, H., & Shin, J. (Dec. 3, 2018). A simple unified framework for detecting out-of-distribution samples and adversarial attacks. Advances in neural information processing systems, 31.

Lichtenstein, M., Sattigeri, P., Feris, R., Giryes, R., & Karlinsky, L. (Aug. 23, 2020). Tafssi: Task-adaptive feature sub-space learning for few-shot classification. In European Conference on Computer Vision (pp. 522-539). Springer, Cham.

Loshchilov, I., & Hutter, F. (Aug. 13, 2016). SGDR: Stochastic gradient descent with warm restarts. arXiv preprint arXiv:1608.03983.

Van der Maaten, L., & Hinton, G. (Nov. 1, 2008). Visualizing data using t-SNE. Journal of machine learning research, 9(11).

Ren, M., Triantafillou, E., Ravi, S., Snell, J., Swersky, K., Tenenbaum, J. B., . . . & Zemel, R. S. (Mar. 2, 2018). Meta-learning for semi-supervised few-shot classification. arXiv preprint arXiv:1803.00676.

Santurkar, S., Tsipras, D., & Madry, A. (Aug. 11, 2020). Breeds: Benchmarks for subpopulation shift. arXiv preprint arXiv:2008.04859.

Sohoni, N., Dunnmon, J., Angus, G., Gu, A., & Ré, C. (Dec. 6, 2020). No subclass left behind: Fine-grained robustness in coarse-grained classification problems. Advances in Neural Information Processing Systems, 33, 19339-19352.

Tian, Y., Wang, Y., Krishnan, D., Tenenbaum, J. B., & Isola, P. (Aug. 23, 2020). Rethinking few-shot image classification: a good embedding is all you need?. In European Conference on Computer Vision (pp. 266-282). Springer, Cham.

Wang, Y., Chao, W. L., Weinberger, K. Q., & van der Maaten, L. (Nov. 12, 2019). Simpleshot: Revisiting nearest- neighbor classification for few-shot learning. arXiv preprint arXiv:1911.04623.

Yang, J., Yang, H., & Chen, L. (Oct. 17, 2021). Towards cross-granularity few-shot learning: coarse-to-fine pseudo- labeling with visual-semantic meta-embedding. In Proceedings of the 29th ACM International Conference on Multimedia (pp. 3005-3014).

* cited by examiner

SUPERCLASS-CONDITIONAL GAUSSIAN MIXTURE MODEL FOR PERSONALIZED PREDICTION ON DIALYSIS EVENTS

RELATED APPLICATION INFORMATION

This application claims priority to U.S. Provisional Patent Application Ser. No. 63/247,335, filed on Sep. 23, 2021, and U.S. Provisional Patent Application Ser. No. 63/397,060, filed on Aug. 11, 2022, incorporated herein by reference in its entirety.

BACKGROUND

Technical Field

The present invention relates to model prediction and more particularly to a superclass-conditional Gaussian mixture model for personalized prediction on dialysis events.

Description of the Related Art

Recently, the tremendous employments of digital systems in hospitals and many medical institutions have brought forth a large volume of healthcare data of patients. The big data are of substantial value, which enables artificial intelligence (AI) to be exploited to support clinical judgement in medicine. As one of the critical themes in modern medicine, the number of patients with kidney diseases has raised social, medical and socioeconomic issues worldwide. Hemodialysis, or simply dialysis, is a process of purifying the blood of a patient whose kidneys are not working normally, and is one of the important renal replacement therapies (RRT). However, dialysis patients at high risk of cardiovascular and other diseases require intensive management on blood pressure, anemia, mineral metabolism, and so on. Otherwise, patients may encounter critical events, such as low blood pressure, leg cramp, and even mortality, during dialysis. Therefore, medical staff must decide to start dialysis from various viewpoints. Some previous reports showed that variable clinical factors were related to dialysis events. Therefore, given the availability of big medical data, it is of paramount significance to develop AI systems for making prognostic prediction scores during the pre-dialysis period on the incidence of events in future dialysis, which can largely facilitate the decision-making processes of medical staffs, and hence reduce the risk of events.

SUMMARY

According to aspects of the present invention, a computer-implemented method for model building is provided. The method includes receiving a training set of medical records and model hyperparameters. The method further includes initializing an encoder as a Dual-Channel Combiner Network (DCCN) and initialize distribution related parameters. The method also includes performing, by a hardware processor, a forward computation to (1) the DCCN to obtain the embeddings of the medical records, and (2) the distribution related parameters to obtain class probabilities. The method additionally includes checking by a convergence evaluator if the iterative optimization has converged. The method further includes performing model personalization responsive to model convergence by encoding the support data of a new patient and using the embeddings and event subtype labels to train a personalized classifier.

According to other aspects of the present invention, a computer program product for model building is provided. The computer program product includes a non-transitory computer readable storage medium having program instructions embodied therewith. The program instructions are executable by a computer to cause the computer to perform a method. The method includes receiving, by a hardware processor of the computer, a training set of medical records and model hyperparameters. The method further includes initializing, by the hardware processor, an encoder as a Dual-Channel Combiner Network (DCCN) and initialize distribution related parameters. The method also includes performing, by the hardware processor, a forward computation to (1) the DCCN to obtain the embeddings of the medical records, and (2) the distribution related parameters to obtain class probabilities. The method additionally includes checking, by the hardware processor, if the iterative optimization has converged. The method further includes performing, by the hardware processor, model personalization responsive to model convergence by encoding the support data of a new patient and using the embeddings and event subtype labels to train a personalized classifier.

According to still other aspects of the present invention, a computer processing system for model building is provided. The computer processing system includes a memory device for storing program code. The computer processing system further includes a hardware processor operatively coupled to the memory device for storing program code to receive a training set of medical records and model hyperparameters. The hardware processor further runs the program code to initialize an encoder as a Dual-Channel Combiner Network (DCCN) and initialize distribution related parameters. The hardware processor also runs the program code to perform a forward computation to (1) the DCCN to obtain the embeddings of the medical records, and (2) the distribution related parameters to obtain class probabilities. The hardware processor additionally runs the program code to check if the iterative optimization has converged. The hardware processor further runs the program code to perform model personalization responsive to model convergence by encoding the support data of a new patient and using the embeddings and event subtype labels to train a personalized classifier.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Embodiments of the present invention are directed to a superclass-conditional Gaussian mixture model for personalized prediction on dialysis events.

Figure 1:
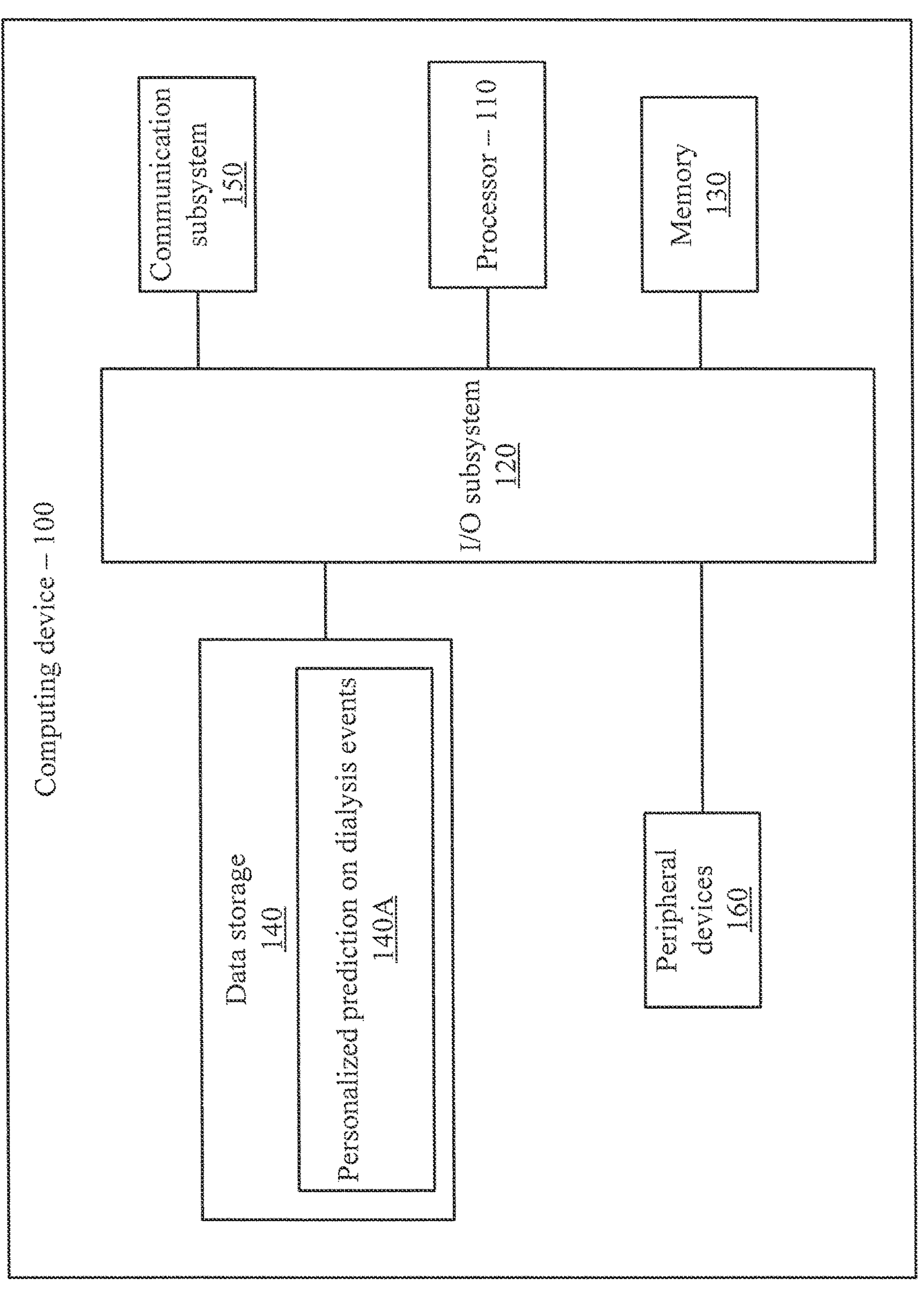
FIG. 1 is a block diagram showing an exemplary computing device, in accordance with an embodiment of the present invention.

Specifically, dialysis patients have regular routine of dialysis sessions with a frequency of 3 times per week. Each session takes approximately 4 hours. The problem to solve is to predict the possibility of the incidence of events in a near future dialysis session for each patient based on the past recording data, FIG. 1 is a block diagram showing an exemplary computing device 100, in accordance with an embodiment of the present invention. The computing device 100 is configured to form and use a superclass-conditional Gaussian mixture model for personalized prediction on dialysis events.

The computing device 100 may be embodied as any type of computation or computer device capable of performing the functions described herein, including, without limitation, a computer, a server, a rack based server, a blade server, a workstation, a desktop computer, a laptop computer, a notebook computer, a tablet computer, a mobile computing device, a wearable computing device, a network appliance, a web appliance, a distributed computing system, a processor-based system, and/or a consumer electronic device. Additionally or alternatively, the computing device 100 may be embodied as a one or more compute sleds, memory sleds, or other racks, sleds, computing chassis, or other components of a physically disaggregated computing device. As shown in FIG. 1, the computing device 100 illustratively includes the processor 110, an input/output subsystem 120, a memory 130, a data storage device 140, and a communication subsystem 150, and/or other components and devices commonly found in a server or similar computing device. Of course, the computing device 100 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 130, or portions thereof, may be incorporated in the processor 110 in some embodiments.

The processor 110 may be embodied as any type of processor capable of performing the functions described herein. The processor 110 may be embodied as a single processor, multiple processors, a Central Processing Unit(s) (CPU(s)), a Graphics Processing Unit(s) (GPU(s)), a single or multi-core processor(s), a digital signal processor(s), a microcontroller(s), or other processor(s) or processing/controlling circuit(s).

The memory 130 may be embodied as any type of volatile or non-volatile memory or data storage capable of performing the functions described herein. In operation, the memory 130 may store various data and software used during operation of the computing device 100, such as operating systems, applications, programs, libraries, and drivers. The memory 130 is communicatively coupled to the processor 110 via the I/O subsystem 120, which may be embodied as circuitry and/or components to facilitate input/output operations with the processor 110 the memory 130, and other components of the computing device 100. For example, the I/O subsystem 120 may be embodied as, or otherwise include, memory controller hubs, input/output control hubs, platform controller hubs, integrated control circuitry, firmware devices, communication links (e.g., point-to-point links, bus links, wires, cables, light guides, printed circuit board traces, etc.) and/or other components and subsystems to facilitate the input/output operations. In some embodiments, the I/O subsystem 120 may form a portion of a system-on-a-chip (SOC) and be incorporated, along with the processor 110, the memory 130, and other components of the computing device 100, on a single integrated circuit chip.

The data storage device 140 may be embodied as any type of device or devices configured for short-term or long-term storage of data such as, for example, memory devices and circuits, memory cards, hard disk drives, solid state drives, or other data storage devices. The data storage device 140 can store program code to form and use a superclass-conditional Gaussian mixture model for personalized prediction on dialysis events. The communication subsystem 150 of the computing device 100 may be embodied as any network interface controller or other communication circuit, device, or collection thereof, capable of enabling communications between the computing device 100 and other remote devices over a network. The communication subsystem 150 may be configured to use any one or more communication technology (e.g., wired or wireless communications) and associated protocols (e.g., Ethernet, InfiniBand®, Bluetooth®, Wi-Fi®, WiMAX, etc.) to effect such communication.

As shown, the computing device 100 may also include one or more peripheral devices 160. The peripheral devices 160 may include any number of additional input/output devices, interface devices, and/or other peripheral devices. For example, in some embodiments, the peripheral devices 160 may include a display, touch screen, graphics circuitry, keyboard, mouse, speaker system, microphone, network interface, and/or other input/output devices, interface devices, and/or peripheral devices. In an embodiment, the peripheral devices include a dialysis machine for performing dialysis on a patient responsive to a system output.

Of course, the computing device 100 may also include other elements (not shown), as readily contemplated by one of skill in the art, as well as omit certain elements. For example, various other input devices and/or output devices can be included in computing device 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized. These and other variations of the processing system 100 are readily contemplated by one of ordinary skill in the art given the teachings of the present invention provided herein.

As employed herein, the term "hardware processor subsystem" or "hardware processor" can refer to a processor, memory (including RAM, cache(s), and so forth), software (including memory management software) or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing elementbased controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), FPGAs, and/or PLAs.

These and other variations of a hardware processor subsystem are also contemplated in accordance with embodiments of the present invention The recording data of dialysis patients mainly constitute four parts: static profiles of the patients (e.g., age, gender, starting time of dialysis, etc.); dialysis measurement records (with a frequency of 3 times/week, e.g., blood pressure, weight, venous pressure, etc.); blood test measurements (with a frequency of 2 times/month, e.g., albumin, glucose, platelet count, etc.); and cardiothoracic ratio (CTR, with a frequency of 1 time/month). The last three parts are dynamic and change over time, so they can be modeled by time series, but with different frequencies.

Building effective AI systems often requires training sufficiently generalizable machine learning models, which often demands immense training data with fine-grained annotations. This need, however, is hard to fulfill in medical areas as exhaustive data labeling requires strong domain-specific knowledge, which is prohibitively costly, and infeasible at a large scale.

Therefore, it is a common practice that during model training, only data with "coarse" labels are available, while later the model may be tested on a finer-grained classification task. For example, in the aforementioned dialysis domain, for model training, binary labels, which mark whether an event has occurred in a dialysis or not, can be collected. In contrast, finer-grained labels that annotate different subtypes of events (e.g., different unstable patterns of blood pressure) are seldom recorded. Whereas, distinguishing different subtypes could facilitate precise diagnoses, given that different patients have different chances of having certain subtypes of events. Hence, it is desirable that a model trained with only coarse (binary) labels can perform well on a finer-grained multi-class (subtypes) task.

Figure 2:
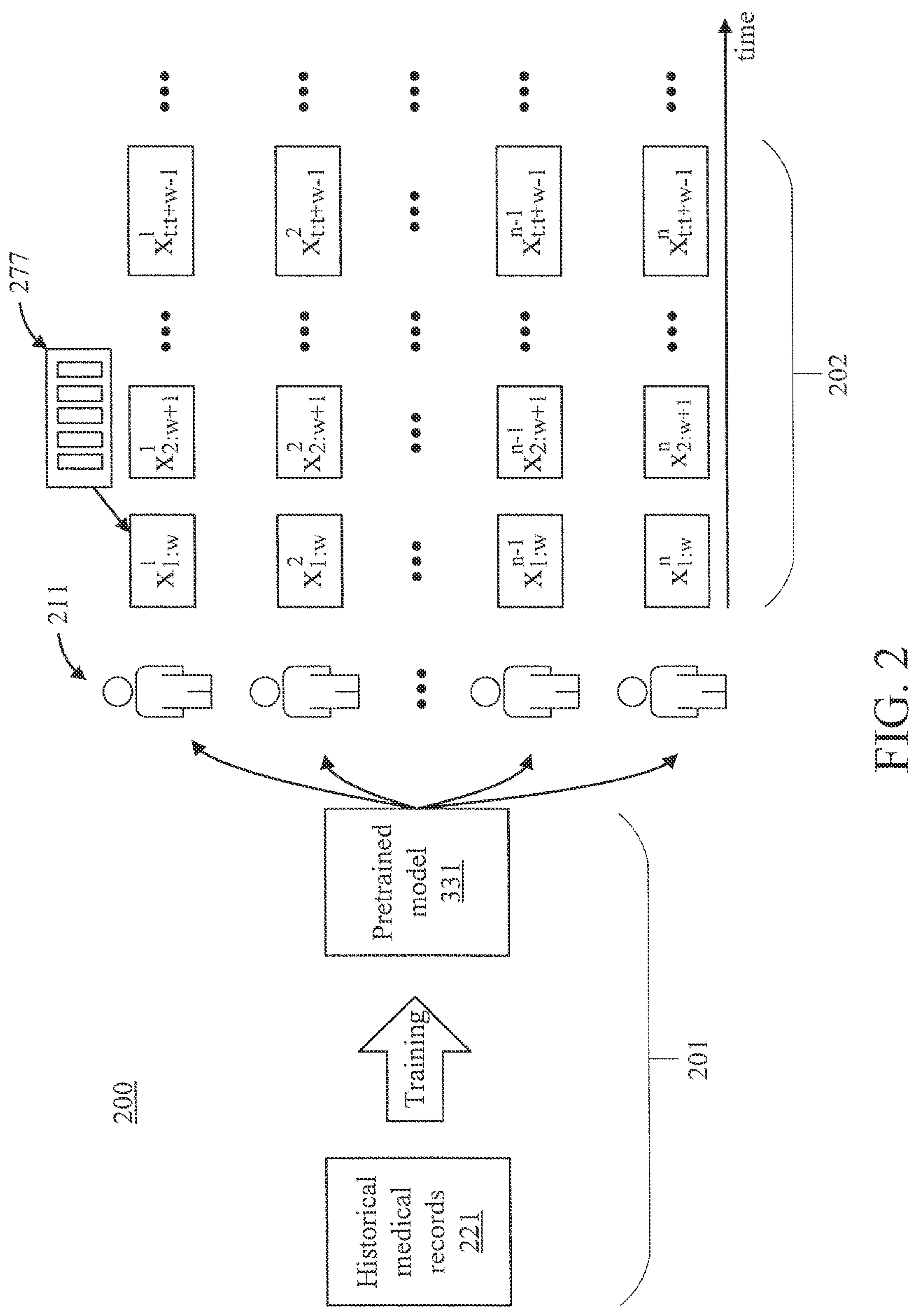
FIG. 2 is a block diagram showing an exemplary framework of model personalization, in accordance with an embodiment of the present invention.

Embodiments of the present invention seek to fill this gap of granularity between the training and testing scenarios. Embodiments of the present invention fit a framework of model personalization, as illustrated in FIG. 2, in accordance with an embodiment of the present invention.

At the pre-training stage 201, only binary labels from historical medical records 221 are used. For every new patient 211, a short period of a few medical records 277 are collected with their fine-grained annotations. These data constitute a support set 202 for adapting a pre-trained model 331 to the specific data distribution of the target patient, for whom the adapted (personalized) model is used for future predictions. Although massive fine-grained annotation is impractical, annotating a few-shot set is feasible. Then at the testing stage, the personalized model is used for predicting event subtypes that are specified in the support set.

The focus of the invention is the pre-training stage. That is, how to get a pretrained model by training a model with coarse labels (denoted as superclasses) so that it can quickly adapt to a new patient's data distribution using a few medical records 277 with fine-grained labels (denoted as subclasses) of that patient, and perform well on event subtype (i.e., subclass) prediction.

This task is challenging because it cannot be trivially solved by regularly training models with coarse supervision, because typical losses for supervised learning aim to maximize inter-class boundaries but neglect intra-class variation. As a result, subclasses may arbitrarily spread within every superclass. The learned feature space only retains attributes for predicting superclasses, but suppresses attributes that may distinguish subclasses.

To address this task, in embodiments of the present invention, a novel machine learning model is provided, which can be trained with the supervision with superclasses, but learns embeddings that are fine-grained so that the pre-trained model can adapt to a fine-grained multi-class task quickly with a few training samples and perform well. The key innovation of the present invention is a general training framework that is characterized by a novel Superclass Conditional Gaussian Mixture model (SCGM), which models the generative process of samples from hierarchies of classes. Its advantage are as follows:

- It explicitly represents the unobserved subclasses by latent variables
- It models the hierarchical structure of subclasses and superclasses
- It is agnostic to the encoder, thus is flexible to different applications
- It only adds a small overhead to an encoder, for parameterizing its distributions, thus is efficient to train
- Its optimization algorithm, an Expectation-Maximization (EM) algorithm, alternately solves model parameters and distribution parameters, which is theoretically principled, and practically stable It is also worth mentioning that the SCGM framework is general and can be applied to other medical records data and data in other domains (i.e., images, texts, etc.) with the use of a proper data encoder. That is, the SCGM framework is compatible with different data encoders while maintaining the spirit of the present invention.

Figure 3:
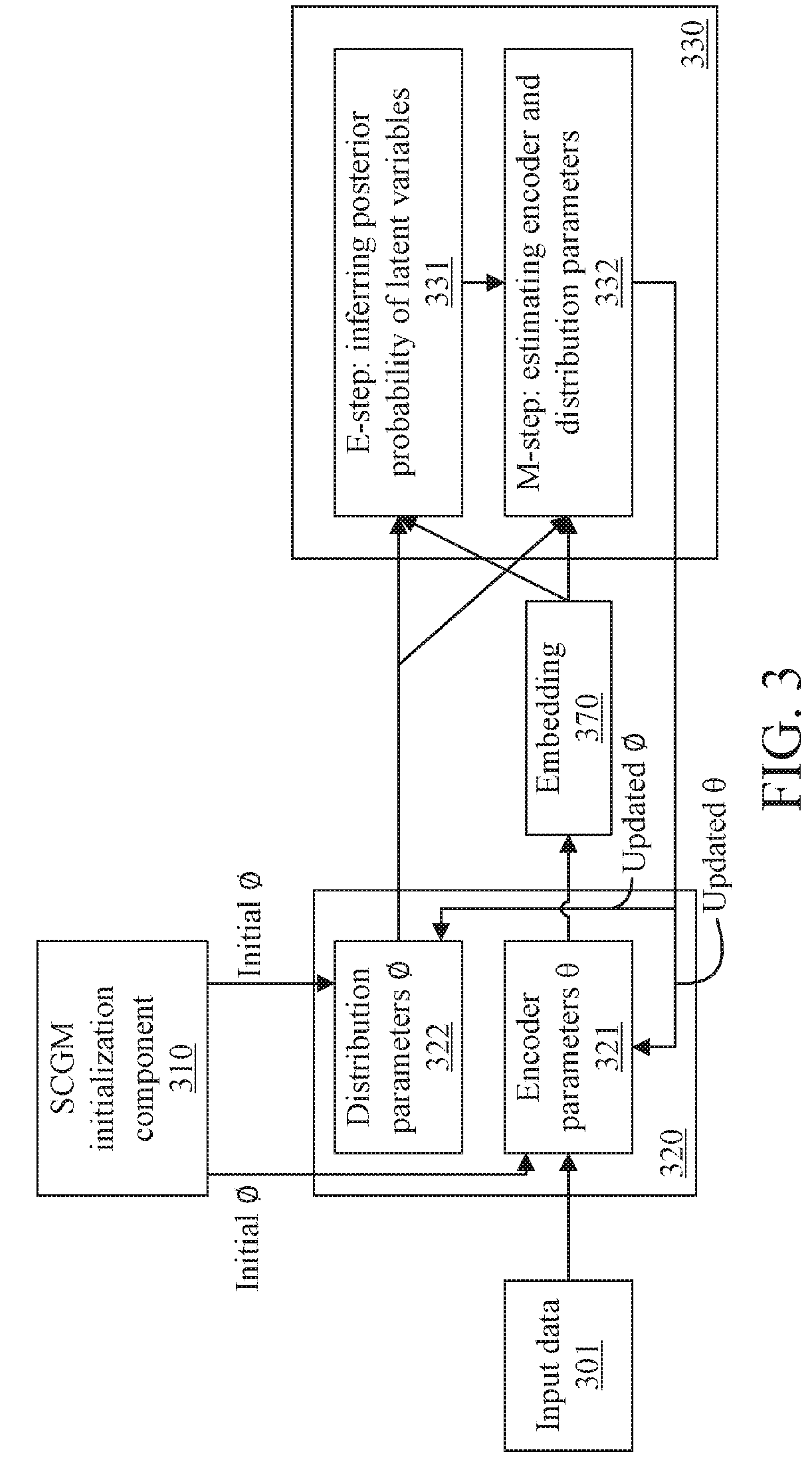
FIG. 3 is a diagram showing an exemplary structure of a Superclass Conditional Gaussian Mixture (SCGM) model, in accordance with an embodiment of the present invention.

FIG. 3 shows the structure of the Superclass Conditional Gaussian Mixture (SCGM) model, in accordance with an embodiment of the present invention. There are three major components: (1) SCGM initialization component 310, (2) SCGM forward computing component 320, and (3) SCGM optimization component 330.

SCGM Initialization Component (310)

The purpose of the SCGM initialization component 310 is to initialize the encoder architecture 320, encoder parameters 321 and distribution parameters 322 related to the computation of SCGM model. The encoder parameters pertain to a neural network for encoding certain type of data. The distribution parameters are Gausssian mixture means, variances, and latent variables.

The Initialization of the Encoder 321

Figure 4:
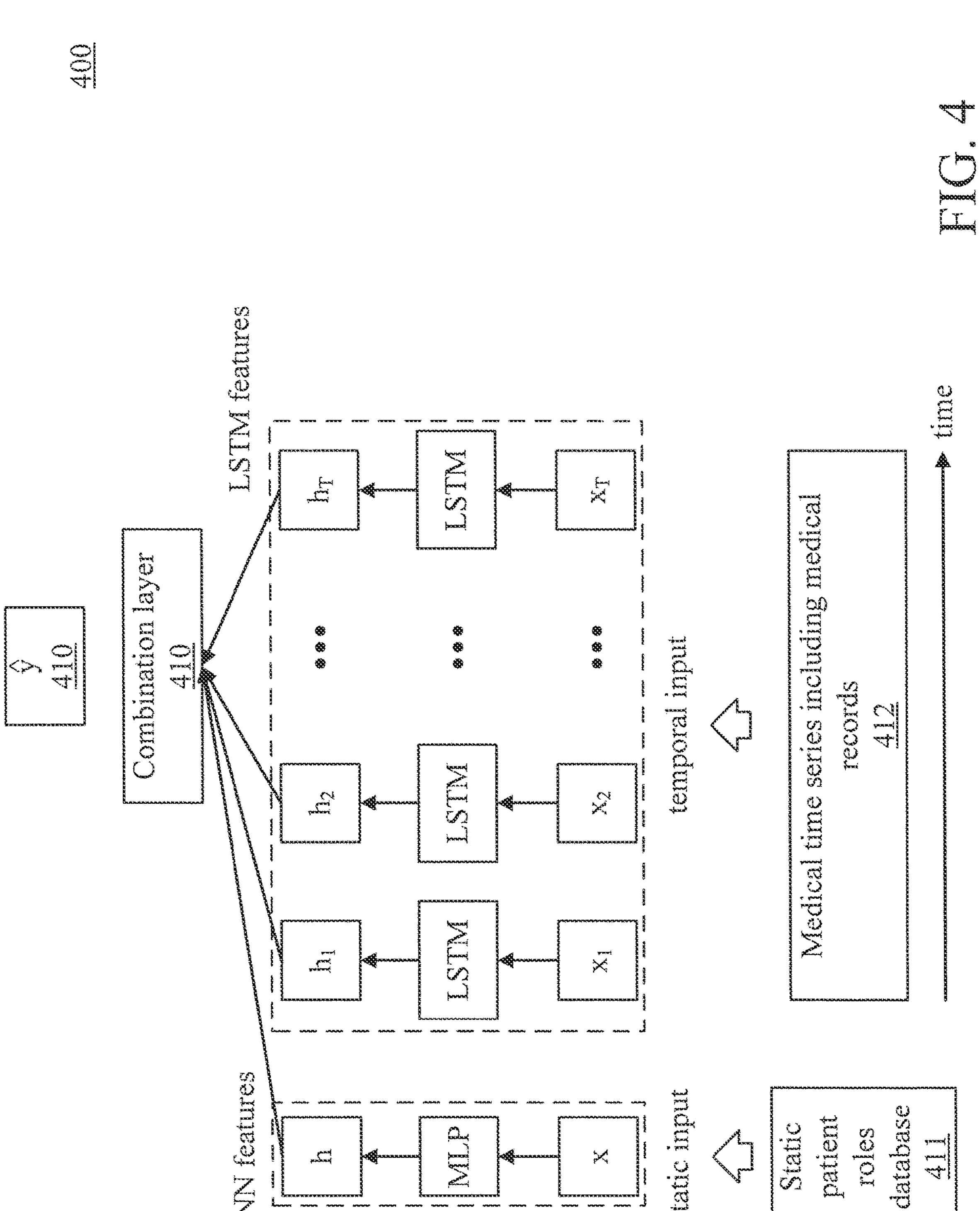
FIG. 4 is a diagram illustrating the encoder architecture 320 of FIG. 3, in accordance with an embodiment of the present invention.

For event subtype prediction, the input data 301 are static patient profiles and medical time series (including medical records), the encoder architecture is a Dual-Channel Combiner Network (DCCN), which is illustrated in FIG. 4, in accordance with an embodiment of the present invention.

The DCCN is effective to process heterogeneous medical records data that usually includes static profiles 411 and time series (i.e., records) 412. It has a static channel realized by a multilayer perceptron (MLP) to encode static features x (e.g., demographic information, infrequent blood test results, etc.) and a temporal channel realized by Long Short-Term Memories (LSTMs) to encode temporal features $x_1$ through $x_T$ (e.g., blood flow, venous pressure, etc.).

The hidden representations (denoted by an "h") output by the two channels are concatenated (or polled using a certain polling method) and further projected to a compact embedding that is used for prediction by the classification head, i.e., the combination layer 410 in FIG. 4, which can be realized by a MLP. An attention layer may be added before the combination layer 410 for weighted combination of the hidden representations from different channels and different time steps. $\hat{Y}$ denotes a prediction of event probability.

All trainable parameters form the encoder parameters θ as illustrated in FIG. 3.

The Initialization of Distribution Parameters

The distribution parameters ϕ 322 include r different means of subclass Gaussian mixture $$\{\mu_j\}_{j=1}^r$$

and c different means of superclass Gaussian mixture $$\{\overline{\mu}_j\}_{j=1}^c,$$

where r is a hyperparameter, c is known from the training dataset. Also there are hyperparameters σ and $\overline{\sigma}$ for representing the variances of the subclass Gaussian mixture distributions, and superclass Gaussian mixture distributions.

The distribution parameters 322 are important to manipulate the embeddings 370 learned from the medical records data, so that SCGM model enables fast adaptation to a fine-grained multi-class (event subtype) task with a few training samples and perform well, which effectively solves the investigated problem as described in A1. The learnable parameters in ϕ 322 will be learned by the M-step 332 in the optimization component 330.

SCGM Forward Computing Component

Here, we first introduce the forward computation of the encoder θ, then introduce the forward computation related to the distribution parameters ϕ.

The Forward Computation of the Encoder 320

This step computes the embeddings of the input medical records. Denoting the DCCN as a parameterized function $f_\theta(\cdot)$, the computation in this step can be represented by the following:

$$v=f_\theta(x_s,[x_1, \ldots, x_T])$$

where $x_s$ is a vector that represents all features in the static profile, $x_t$ is a vector that represents all features in the medical records at time step t, $[x_1, \ldots, x_T]$ represents all medical records from time step 1 to T. v is a low-dimensional vector representing the embedding from the input, which will be used for downstream computation.

The Forward Computation Related to the Distribution Parameters

The distribution parameters $$\phi = \{\{\mu_j\}_{j=1}^r, \{\overline{\mu}_j\}_{j=1}^c\}$$

will be used to compute several probabilities.

$$p_\phi(y_i|z_i) = \frac{\exp\left(\frac{\mu_{z_i}^T \cdot \overline{\mu}_{y_i}}{\overline{\sigma}^2}\right)p(y_i)}{\sum_{y_i'=1}^c \exp\left(\frac{\mu_{z_i}^T \cdot \overline{\mu}_{y_{i'}}}{\overline{\sigma}^2}\right)p(y_i')}$$

$$p_{\theta,\phi}(z_i|v_i) = \frac{\exp\left(\frac{v_i^T \cdot \mu_{z_i}}{\sigma^2}\right)\pi_{z_i}^i}{\sum_{y_i'=1}^c \exp\left(\frac{v_i^T \cdot \mu_{z_{i'}}}{\sigma^2}\right)\pi_{z_i}^i} \text{ where}$$

$$\pi_{z_i}^i = \frac{\exp\left(\frac{(\mu_{z_i} - \overline{\mu}_{y_i})^T \cdot (\mu_{z_i} - \overline{\mu}_{y_i})}{\overline{\sigma}^2}\right)}{\sum_{z_i'=1}^r - \frac{1}{2}\exp\left(\frac{(\mu_{z_{i'}} - \overline{\mu}_{y_i})^T \cdot (\mu_{z_i'} - \overline{\mu}_{y_i})}{\overline{\sigma}^2}\right)}$$

where the subscript i indicates the variable for the i-the patient. $p(y_i)$ is a prior on $y_i$, which can be drawn from a Dirichlet distribution Dir(α), and α can be estimated by the ratio of different labels in the training dataset. $p(y_i)$ can also be specified as a uniform prior $$\frac{1}{c},$$

for unknown datasets and better generalization.

These computation derives a generative process of the embeddings from a superclass-conditional Gaussian mixture (SCGM) distribution.

Figure 5:
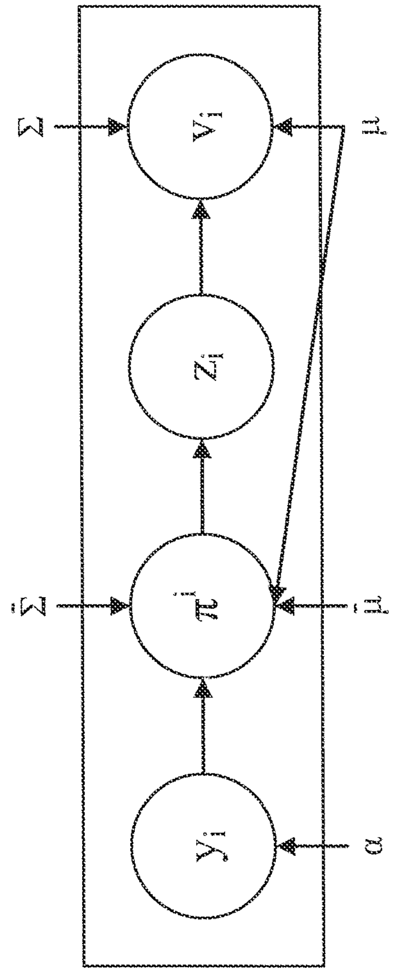
FIG. 5 is a graphical model of the SCGM model, in accordance with an embodiment of the present invention.

FIG. 5 is a graphical model 500 of the SCGM model, in accordance with an embodiment of the present invention.

The graphical model 500 in FIG. 5 summarizes the relationship and computational flow among different model variables and parameters in the present SCGM forward computing component.

$y_i$ represents the superclass label of the i-th sample, i.e., a segment of medical records.

$\pi^i$ is a vector of the dynamic mixture probabilities (a vector of the probability of each mixture component) of the i-th sample.

$z_i$ is the latent variable of the i-th sample, which indicates to which subclass the i-th sample belongs.

$v_i$ is the embedding of the i-th sample, i.e., the output of the encoder after inputting the i-th sample.

α is a parameter of the prior distribution of $y_i$.

$\overline{\mu}$ is a vector of the means of the Gaussian mixture of the superclasses.

$\overline{\Sigma}$ is a vector of the variances of the Gaussian mixture of the superclasses.

μ is a vector of the means of the Gaussian mixture of the subclasses.

Σ is a vector of the variances of the Gaussian mixture of the subclasses.

SCGM Optimization Component 330

The SCGM optimization component 330 has two alternately updated steps, E-step 331 for inferring the posterior probability $q(z_i|v_i,y_i)$, which indicates the membership of an embedding $v_i$ to a subclass $z_i$, and M-step 332 for estimating the model parameters θ and ϕ.

The objective function to optimize in this step is as follows:

$$\frac{1}{2}\sum_{i=1}^{n}\mathbb{E}_{q(z_i|v_i,y_i)}[\log p_\phi(y_i|z_i)+\log p_{\theta,\phi}(z_i|v_i)-\log q(z_i|v_i,\ y_i)] \tag{1}$$

where the probabilities in the bracket are specified above.

The E-Step Optimization

This step is to infer $q(z_i|v_i,y_i)$ while fixing model parameters θ and ϕ. $q(z_i|v_i,y_i)$ represents the membership probability of an embedding $v_i$ to a subclass $z_i$. The corresponding optimization problem in this step that is derived from Equation (1) is as follows:

$$\min_{Q\in\mathcal{Q}} -\frac{1}{n}\left(Tr\left(Q^T\log P\right)+\frac{1}{\lambda}H(Q)\right),$$

$$\text{where } \mathcal{Q}=\left\{Q\in\mathbb{R}_+^{r\times n}\middle|Q1_n=\frac{1}{r}1_r,\ Q^T1_r=\frac{1}{n}1_n\right\}$$

where Q is a matrix including all probabilities $q(z_i|v_i,y_i)$ for different i, and P is a matrix including the values that sum the first two terms in the brackets in Equation (1) (excluding the last term $\log(q(z_i|v_i,y_i))$). The constraint Q enforces an equal partition constraint on subclasses, so that the problem is efficiently solvable.

To solve this problem, we use an iterative Sinkhorn-Knopp algorithm, which is efficient and stable. After obtaining the optimal solution Q*, rounding its value and using the discrete codes make the training algorithm more stable.

The M-Step Optimization

This step is to estimate the encoder parameters θ and the distribution related parameters ϕ, while fixing the posterior probability $q(z_i|v_i,y_i)$ that is obtained from the E-step. The model parameters can be efficiently solved by stochastic gradient descent (SGD). The corresponding optimization problem in this step is derived from Equation (1) as follows:

$$\ell(D_{train};\theta,\phi)=\ell_{CE}\left(D_{train};\theta,\{\mu_j\}_{j=1}^{c}\right)+\gamma\ell_{\phi,\theta}(D_{train};\theta,\phi)$$

where $l_{CE}$ is the cross-entropy loss on the predicted superclass from the embeddings and the superclass labels, which is added for better performance, and the second term is as follows:

$$\ell_{\phi,\theta}=-\frac{1}{n}\sum_{i=1}^{n}q(z_i|v_i,\ y_i)\left[\log\frac{\exp\left(\mu_{z_i}^T\cdot\frac{\overline{\mu}_{y_i}}{\sigma^2}\right)p(y_i)}{\sum_{y_i'=1}^{c}\exp\left(\mu_{z_i}^T\cdot\frac{\overline{\mu}_{y_i}}{\sigma^2}\right)p(y_i)}+\log\frac{\exp\left(v_i^T\cdot\frac{\mu_{z_i}}{\sigma^2}\right)\pi_{z_i}^i}{\sum_{z_i'=1}^{c}\exp(v_i^T\cdot\mu_{z_i'}/\sigma^2)\pi_{z_i'}^i}\right]$$

where the computation of $p(y_i)$ and $$\pi_{z_i}^i$$

have been discussed herein. In the above optimization problem, γ is a trade-off hyperparameter.

After the SGD optimization is done, as illustrated in FIG. 3, the updated model parameters θ and ϕ are sent to the SCGM forward computing component (200) to update embeddings and related probabilities as discussed herein. The updated embeddings and probabilities then will be used to optimize the objective functions in the E-step and M-step of the SCGM optimization component (300). This iterative process will converge. After its convergence, we obtain the final model parameters θ and ϕ, that enables obtaining fine-grained embeddings using the encoder $f_\theta(\cdot)$, which is the DCCN as introduced above, for model personalization and event subtype prediction in the way as illustrated in FIG. 2.

At the pre-training stage, only binary labels are used for learning θ and ϕ. For every new patient, a short period of a few medical records are collected with their fine-grained annotations. These data constitute a support set for adapting a pre-trained model to the specific data distribution of the target patient, for whom the adapted (personalized) model is used for future predictions. At the testing stage, the personalized model is used for predicting event subtypes that are specified in the support set.

Figure 6:
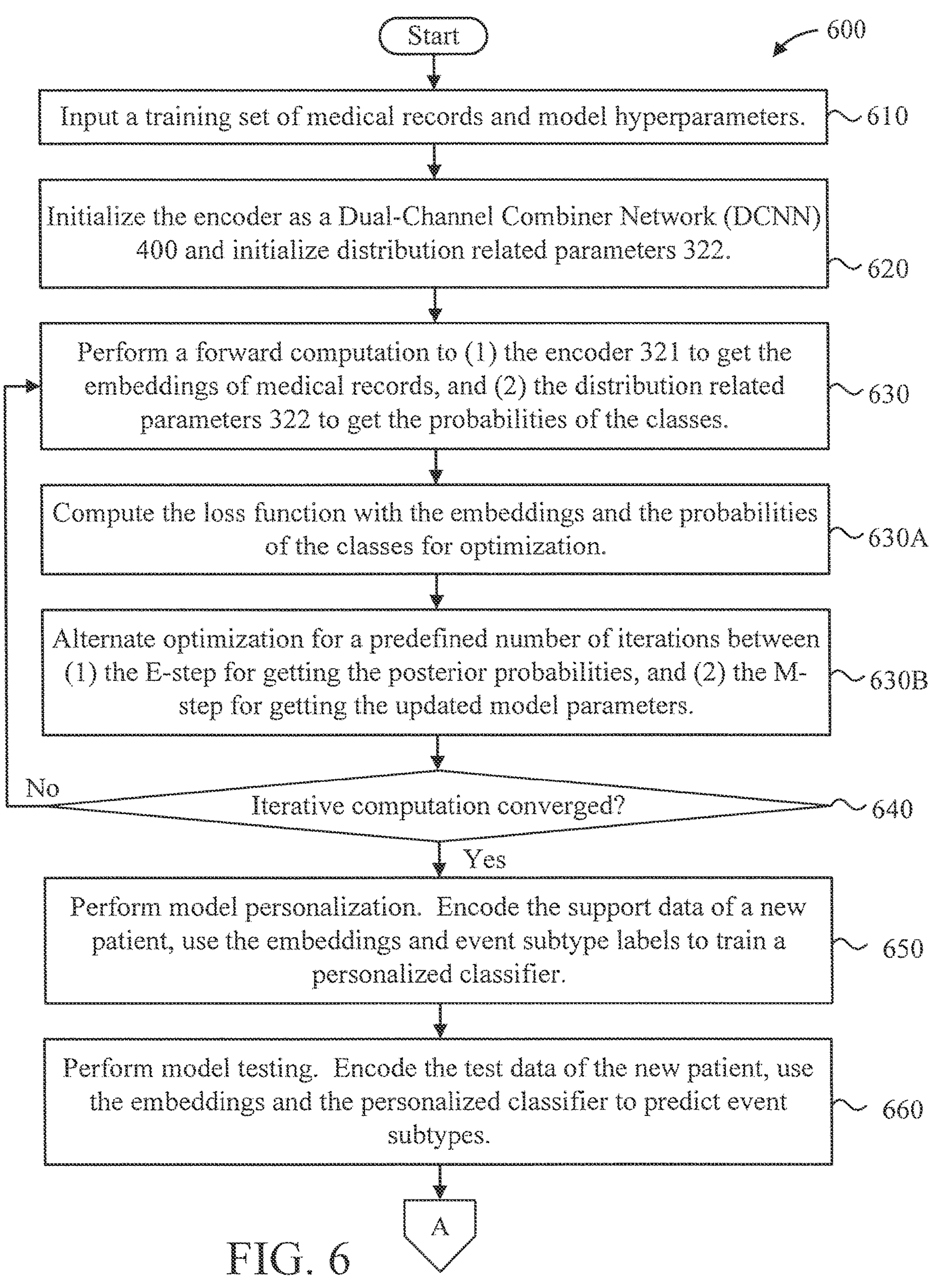
FIGS. 6-7 show an exemplary method for personalized prediction on dialysis events, in accordance with an embodiment of the present invention.
Figure 7:
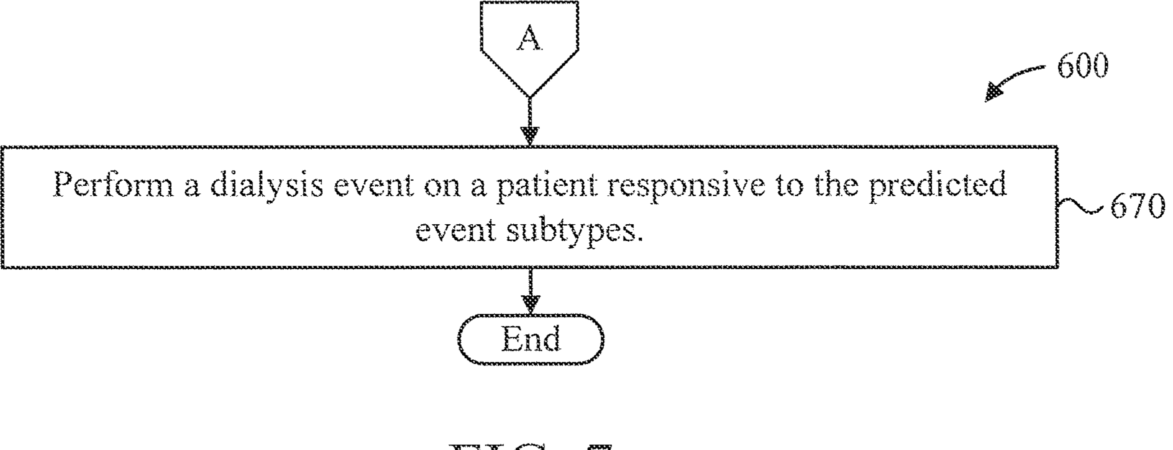

FIGS. 6-7 show an exemplary method 600 for personalized prediction on dialysis events, in accordance with an embodiment of the present invention.

At block 610, input a training set of medical records and model hyperparameters.

At block 620, initialize the encoder as a Dual-Channel Combiner Network (DCCN) 400 and initialize distribution related parameters 322.

At block 630, perform a forward computation to (1) the encoder 321 to get the embeddings of medical records, and (2) the distribution related parameters 322 to get the probabilities of the classes.

In an embodiment, block 630 can include blocks 630A through 630B.

At block 630A, compute the loss function with the embeddings and the probabilities of the classes for optimization.

At block 630B, alternate optimization for a predefined number of iterations between (1) the E-step for getting the posterior probabilities, and (2) the M-step for getting the updated model parameters.

At block 640, check by a convergence evaluator if the iterative optimization has converged. If not, return to step 630. Otherwise, save the model and proceed to step 650.

At block 650, perform model personalization. Encode the support data of a new patient, use the embeddings and event subtype labels to train a personalized classifier.

At block 660, perform model testing. Encode the test data of the new patient, use the embeddings and the personalized classifier to predict event subtypes. Event subtypes can include, for example, but are not limited to muscle cramp, perspiration, dizziness, hypotension, respectively.

At block 670, perform a dialysis event on a patient responsive to the predicted event subtypes. Based on the predicted event subtypes, the physicians can better assess the risk for deciding whether to perform a hemodialysis (depending on the impacts of the event subtypes), and if perform a dialysis, what precautions to do for the patient regarding the dialysis.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A computer-implemented method for model building, comprising:

receiving a training set of medical records and model hyperparameters, wherein the training set of medical records has coarse labels;

initializing an encoder as a Dual-Channel Combiner Network (DCCN) and initialize distribution related parameters, wherein the distribution related parameters comprise learnable subclass Gaussian mixture means and superclass Gaussian mixture means;

performing, by a hardware processor, a forward computation to (1) the DCCN to obtain the embeddings of the medical records, and (2) the distribution related parameters to obtain class probabilities, by modeling each embedding as being generated from a superclass-conditional Gaussian mixture distribution in which subclass membership is represented as an unobserved latent variable;

iteratively optimizing, by alternating between a step that assigns subclass membership probabilities to each embedding, and a step that updates encoder parameters and the distribution related parameters based on those assignments;

saving a model if the iterative optimization has converged; and performing model personalization on the saved model responsive to convergence by encoding support data of a new patient and using embeddings of the support data and event subtype labels of the support data to train a personalized classifier.

2. The computer-implemented method of claim 1, wherein performing a forward computation comprises computing a loss function with the embeddings and the class probabilities for optimization.

3. The computer-implemented method of claim 1, further comprising performing model testing by encoding test data of the new patient and using the embeddings and the personalized classifier to predict event subtypes.

4. The computer-implemented method of claim 3, further comprising performing a dialysis event on a patient responsive to the predicted event subtypes.

5. The computer-implemented method of claim 1, wherein the DCCN includes a static channel for encoding static patient profiles, and a temporal channel to encode temporal patient status features, wherein outputs of the static channel and the temporal channel are concatenated and projected to a compact embedding used for prediction by a combination layer of the DCCN.

6. The computer-implemented method of claim 5, wherein the static channel comprises a multilayer perceptron (MLP), and wherein the temporal channel comprises one or more Long Short-Term Memories (LSTMs).

7. A non-transitory computer program product for model building, the computer program product comprising a non-transitory computer readable storage medium having program instructions embodied therewith, the program instructions executable by a computer to cause the computer to perform a method comprising:

receiving, by a hardware processor of the computer, a training set of medical records and model hyperparameters, wherein the training set of medical records has coarse labels;

initializing, by the hardware processor, an encoder as a Dual-Channel Combiner Network (DCCN) and initialize distribution related parameters, wherein the distribution related parameters comprise learnable subclass Gaussian mixture means and superclass Gaussian mixture means;

performing, by the hardware processor, a forward computation to (1) the DCCN to obtain the embeddings of the medical records, and (2) the distribution related parameters to obtain class probabilities, by modeling each embedding as being generated from a superclass-conditional Gaussian mixture distribution in which subclass membership is represented as an unobserved latent variable;

iteratively optimizing, by the hardware processor, by alternating between a step that assigns subclass membership probabilities to each embedding and a step that updates encoder parameters and the distribution related parameters based on those assignments;

saving a model, by the hardware processor, if the iterative optimization has converged; and performing, by the hardware processor, model personalization on the saved model responsive to convergence by encoding support data of a new patient and using embeddings of the support data and event subtype labels of the support data to train a personalized classifier.

8. The computer program product of claim 7, wherein performing a forward computation comprises computing a loss function with the embeddings and the class probabilities for optimization.

9. The computer program product of claim 7, further comprising performing model testing by encoding test data of the new patient and using the embeddings and the personalized classifier to predict event subtypes.

10. The computer program product of claim 9, further comprising performing a dialysis event on a patient responsive to the predicted event subtypes.

11. The computer program product of claim 7, wherein the DCCN includes a static channel for encoding static patient profiles, and a temporal channel to encode temporal patient status features, wherein outputs of the static channel and the temporal channel are concatenated and projected to a compact embedding used for prediction by a combination layer of the DCCN.

12. The computer program product of claim 11, wherein the static channel comprises a multilayer perceptron (MLP), and wherein the temporal channel comprises one or more Long Short-Term Memories (LSTMs).

13. A computer processing system for model building, comprising:

a memory device for storing program code; and a hardware processor operatively coupled to the memory device for storing program code to receive a training set of medical records and model hyperparameters, wherein the training set of medical records has coarse labels;

initialize an encoder as a Dual-Channel Combiner Network (DCCN) and initialize distribution related parameters, wherein the distribution related parameters comprise learnable subclass Gaussian mixture means and superclass Gaussian mixture means;

perform, by a hardware processor, a forward computation to (1) the DCCN to obtain the embeddings of the medical records, and (2) the distribution related parameters to obtain class probabilities, by modeling each embedding as being generated from a superclass-conditional Gaussian mixture distribution in which subclass membership is represented as an unobserved latent variable;

iteratively optimize, by the hardware processor, by alternating between a step that assigns subclass membership probabilities to each embedding and a step that updates encoder parameters and the distribution related parameters based on those assignments;

save a model if the iterative optimization has converged; and perform model personalization on the saved model responsive to convergence by encoding support data of a new patient and using embeddings of the support data and event subtype labels of the support data to train a personalized classifier.

14. The computer processing system of claim 13, wherein performing a forward computation comprises computing a loss function with the embeddings and the class probabilities for optimization.

15. The computer processing system of claim 13, wherein the processor further runs the program code to perform model testing by encoding test data of the new patient and using the embeddings and the personalized classifier to predict event subtypes.

16. The computer processing system of claim 15, wherein the processor further runs the program code to control performing a dialysis event on a patient responsive to the predicted event subtypes.

17. The computer processing system of claim 13, wherein the DCCN includes a static channel for encoding static patient profiles, and a temporal channel to encode temporal patient status features, wherein outputs of the static channel and the temporal channel are concatenated and projected to a compact embedding used for prediction by a combination layer of the DCCN.

* * * * *